United States Patent [19]

Sulkowski et al.

[11] 3,931,218
[45] Jan. 6, 1976

[54] 2-(N-ALKYL-2-IMIDAZOLIN-2-YL)BENZOPHENONES AND PROCESS FOR THEIR PREPARATION

[75] Inventors: Theodore S. Sulkowski, Wayne; Albert A. Mascitti, Norristown, both of Pa.

[73] Assignee: American Home Products Corporation, New York, N.Y.

[22] Filed: Aug. 7, 1974

[21] Appl. No.: 495,262

Related U.S. Application Data

[63] Continuation-in-part of Ser. No. 332,535, Feb. 14, 1973, abandoned.

[52] U.S. Cl.... 260/309.6; 260/343.2 R; 260/556 B; 424/273
[51] Int. Cl.² ........................................ C07D 49/34
[58] Field of Search ................................ 260/309.6

[56] References Cited
UNITED STATES PATENTS

| | | | |
|---|---|---|---|
| 2,214,152 | 9/1940 | Wilkes | 260/309.6 |
| 3,202,674 | 8/1965 | Langis et al. | 260/309.6 |
| 3,408,361 | 10/1968 | Mannheimer | 260/309.6 |
| 3,717,658 | 2/1973 | Metlesics et al. | 260/309.6 |

FOREIGN PATENTS OR APPLICATIONS

| | | | |
|---|---|---|---|
| 1,187,009 | 4/1970 | United Kingdom | 260/309.6 |
| 1,258,946 | 12/1971 | United Kingdom | 260/309.6 |

OTHER PUBLICATIONS

Hoffman, Imidazole and its Derivatives, Part I, pp. 213–219, N.Y., Interscience, 1953.

Primary Examiner—Ethel G. Love
Attorney, Agent, or Firm—Stephen Venetianer

[57] ABSTRACT 2-(N-alkyl-2-imidazolin-2-yl)-benzophenones are prepared by reaction of the ψ-acid chloride of an o-aroyl benzoic acid with an $N^1$-alkyl-$N^2$-tosyl diamine and heating the resulting benzoyl benzamide product with sulfuric acid. The compounds demonstrate hypoglycemic antireserpine, antiulcerogenic or antiarrhythmic activity.

25 Claims, No Drawings

2-(N-ALKYL-2-IMIDAZOLIN-2-YL)BENZOPHENONES AND PROCESS FOR THEIR PREPARATION

PRIOR APPLICATION

This application is a continuation-in-part of our co-pending application Ser. No. 332,535, filed Feb 14, 1973, now abandoned.

DESCRIPTION OF THE INVENTION 2-(N-alkyl-2-imidazolin-2-yl)-benzophenones are prepared according to this invention by contacting the appropriate benzoyl benzamide with sulfuric acid and subsequently treating the product with a base. Thus 2-(N-alkyl-2-imidazolin-2-imidazolin-2-yl)-benzophenones of the formula

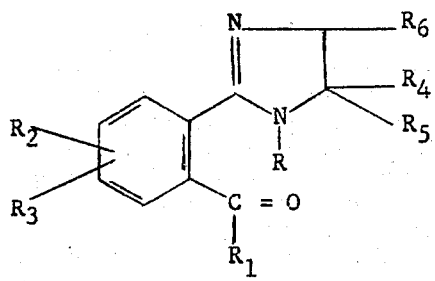

wherein R is (lower)alkyl; $R_1$ is selected from the group consisting of phenyl, monohalophenyl, dihalophenyl, mono(lower)alkylphenyl, di(lower)-alkylphenyl, trifluoromethylphenyl, mono(lower) alkoxyphenyl, di(lower)alkoxyphenyl, thienyl, pyridyl, furyl, and tetrahydro-2-naphthyl; $R_2$ is selected from the group consisting of hydrogen, halogen, amino, (lower)alkylamino, (lower)alkyl and (lower) alkoxy; $R_3$ is hydrogen when $R_2$ and $R_3$ are dissimilar and when $R_2$ and $R_3$ are the same they are both selected from the group consisting of hydrogen, halogen, (lower)alkyl and (lower)alkoxy; $R_4$ and $R_5$ are each hydrogen or lower alkyl and attached to the same carbon atom; and $R_6$ is hydrogen or (lower) alkyl are obtained when a benzoyl benzamide of the formula

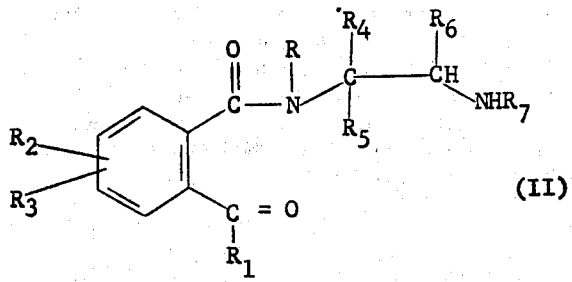

wherein R, $R_1$, $R_2$, $R_3$, $R_4$, $R_5$ and $R_6$ are as defined above and $R_7$ is selected from the group consisting of lower alkylsulfonyl, phenylsulfonyl, monohalophenylsulfonyl, dihalophenylsulfonyl, mono(lower)alkylphenylsulfonyl, di(lower)alkylphenylsulfonyl and lower alkoxyphenylsulfonyl, is contacted with sulfuric acid of from about 90 to 100% concentration, preferably heated on a steam bath from 0.25 to 0.75 hour and allowed to stand at room temperature for from 4 to 24 hours, preferably 15 to 18 hours. The reaction mixture is worked up conventionally such as by quenching with water and adjusting the pH to above 7 with a base to precipitate the product of formula (I) in the form of the free base which can then be reacted with a pharmaceutically acceptable acid to form the acid addition salt.

Products of formula (I) wherein each of R, $R_4$, $R_5$ and $R_6$ is hydrogen are disclosed and claimed in U.S. Pat. No. 3,763,178 granted Oct. 2, 1973.

Products of formula (I) wherein each of $R_4$ and $R_5$ is lower alkyl and each of R and $R_6$ is hydrogen are disclosed in U.S. Pat. No. 3,802,155, granted Apr. 9, 1974.

Thus the 2-(N-alkyl-2-imidazolin-2-yl)-benzophenones of formula (I) are novel including those wherein R is lower alkyl, $R_4$, $R_5$ and $R_6$ being hydrogen, those wherein R and $R_4$ are lower alkyl, $R_5$ and $R_6$ being hydrogen, those wherein R and $R_6$ are lower alkyl, $R_4$ and $R_5$ being hydrogen, those wherein R, $R_4$ and $R_5$ are lower alkyl, $R_6$ being hydrogen, and those wherein R, $R_4$, $R_5$ and $R_6$ are all lower alkyl. The intermediate compounds of formula (II) are also novel.

The intermediate benzoyl benzamides are prepared by reaction of the $\psi$-acid chloride of an appropriate o-aryl benzoic acid of the formula

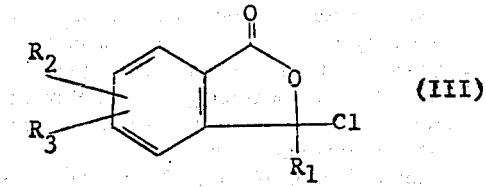

wherein $R_1$, $R_2$ and $R_3$ are as above identified with an $N^1$-alkyl-$N^2$-tosyl diamine of the formula

wherein R, $R_4$, $R_5$, $R_6$ and $R_7$ are as above identified. The reaction can be carried out in pyridine or in a solvent such as dichloromethane in the presence of a base such as triethyl amine, pyridine or N,N-dimethyl aniline. Other inert solvents include toluene, benzene, chloroform, diethyl ether, acetone and the like.

The materials of formula (III) are readily prepared from the keto acids by standard procedures well known to the art.

The materials of formula (IV) are prepared either directly by reaction of the appropriate diamine with the appropriate tosyl chloride

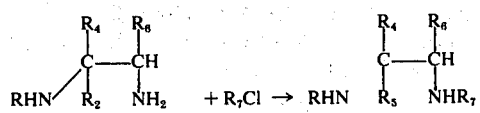

or by reduction of the appropriate tosyl amino acid amide

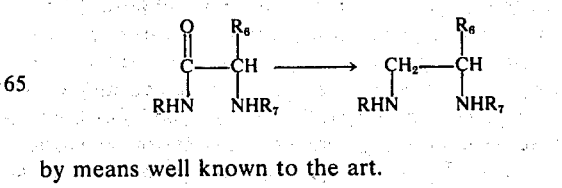

by means well known to the art.

As employed herein the term (lower)alkyl includes straight and branched chain hydrocarbon moieties of from 1 to about 4 carbon atoms such as methyl, ethyl, propyl, i-propyl and butyl. The term (lower)alkoxy includes hydrocarbonoxy groups which contains from 1 to about 6 carbon atoms such as methoxy ethoxy, propoxy, butoxy and hexoxy. The term "halogen" and "halo" as used herein include bromine, fluorine, chlorine and iodine.

The processes of this invention and the new and novel compounds prepared thereby are illustrated by the following examples.

EXAMPLE I

A solution of 65 grams of p-toluenesulfonyl chloride in 125 ml. of dichloromethane was added dropwise with stirring to a solution of 100 grams of N-isopropylethylenediamine in 150 ml. of dichloromethane. Following completion of addition the mixture was stirred one-half hour at room temperature, then heated in a steam bath for 45 minutes. The mixture was evaporated to dryness in vacuo. The residue was triturated with sodium carbonate solution then dissolved in a mixture of ethyl acetate and water. The ethyl acetate portion was extracted with saturated sodium carbonate solution and water. After drying the ethyl acetate portion over magnesium sulfate, the solvent was removed in vacuo. The solid residue was recrystallized from ethyl acetate-hexane to obtain N-[2-(isopropylamino)ethyl]-p-toluenesulfonamide, m.p. 76°–8°C.

Anal. Calc'd for $C_{12}H_{20}N_2SO_2$: C, 56.22; H, 7.87; N, 10.93; S, 12.51. Found: C, 56.43; H, 8.15; N, 10.92; S, 12.60

EXAMPLE II

Twenty-three grams of ψ-acid chloride of 0-(p-chlorobenzoyl)benzoic acid (W. Graf., et. al., Helv. Chim. Acta, 42, 1085) was dissolved in 75 ml. of acetone and added dropwise to a stirred solution of 20.5 grams of N-[2-(isopropylamino) ethyl]-p-toluenesulfonamide in 150 ml. of pyridine. After addition was completed, the solution was warmed in a steam bath for one-half hour, then evaporated to dryness. The residue was dissolved in ethyl acetate and extracted successively with water, saturated sodium carbonate solution, 20% hydrochloric acid, and water. The ethyl acetate portion was dried over magnesium sulfate then evaporated to dryness. The solid was slurried with ethanol and separated by filtration to obtaian 2-(p-chlorobenzoyl)-N-[2-(p-toluenesulfonamido)ethyl]-N-isopropylbenzamide, m.p. 149°–152°C. Analytical sample was prepared by recrystallization from ethanol, m.p. 150°–152°C.

Anal. Calc'd for $C_{26}H_{27}N_2ClSO_4$: C, 62.58; H, 5.45; N, 5.61; Cl, 7.11; S, 6.43. Found: C, 62.67; H, 5.53; N, 5.55; Cl, 7.11; S, 6.14.

EXAMPLE III

Eighteen grams of 2-(p-chlorobenzoyl)-N-[2(p-toluenesulfonamido)ethyl]N-isopropylbenzamide and 65 ml. of 90% (v/v) sulfuric acid were mixed together and heated in a steam bath for thirty minutes. The solution was left standing at room temperature for 17 hours. The mixture was quenched with 800 ml. of ice water and extracted with ethyl acetate. The aqueous portion was cooled and made basic with 50% sodium hydroxide solution. The mixture was extracted with ethyl acetate. The organic portion was extracted with water then dried over magnesium sulfate. The solvent was removed in vacuo. The residue was recrystallized from ethyl acetate-hexane to obtain 4'-chloro-2-(1-isopropyl-2-imidazolin-2-yl)benzophenone, m.p. 114°–117°C. Anal. Calc'd for $C_{19}H_{19}N_2ClO$: C, 69.82; H, 5.86; N, 8.57; Cl, 10,85. Found: C, 69.62; H, 6.05; N, 8.35; Cl, 10.87.

The hydrochloride was prepared by saturating an ethanol solution of the base with hydrogen chloride. The solvent was removed in vacuo. The residue was recrystallized from ethanolethyl acetate, m.p. 229°–231°C.

Anal. Calc'd for $C_{19}H_{19}N_2ClO \cdot HCl$: C, 62.81; H, 5.55; N, 7.71; Cl, 19.52. Found: C, 62.69; H, 5.62; N, 7.56; Cl, 19.39.

Infra red absorption (KBr) 1663 cm$^{-1}$.
UV (95% EtOH) max. 264 $\mu$ ($\epsilon$ = 16,900).

EXAMPLE IV

A. Twenty-five grams of N-acetyl-N'-p-toluenesulfonyl ethylenediamine (L. H. Amunsen, et. al., J. Am. Chem. Soc., 62, 2811) was added in portions to a stirred suspension of 7 grams of lithium aluminum hydride in 500 ml. of anyhdrous ether. The mixture was refluxed for four additional hours, the excess lithium aluminum hydride decomposed by dropwise addition of water and the mixture filtered. The solvent was separated and the filter cake was extracted with hot ethyl acetate. The organic portions were combined and evaporated to dryness. The viscous oily residue was dissolved in 50 ml. of ethanol and saturated with hydrogen chloride. The solvent was removed in vacuo. The solid was washed with a mixture of ethyl acetate-acetone and dried to obtain N-[2-(ethylamino)ethyl]-p-toluenesulfonamide hydrochloride, m.p. 138°–140°C.

Anal. Calc'd for $C_{11}H_{18}N_2SO_2 \cdot HCl$: C, 47.38; H, 6.87; N, 10.05; Cl, 12.72; S, 11.50. Found: C, 47.28; H, 6.83; N, 9.95; Cl, 12.80; S, 11.23.

B. A solution of 95 grams of p-toluenesulfonyl chloride in 175 ml. of pyridine was added dropwise to a stirred solution of 135 grams of N-ethyl ethylenediamine in 250 ml. of pyridine cooled in an ice bath. After addition was completed, the mixture was stirred one-half hour at room temperature then heated in a steam bath for one-half hour. The solvent was removed in vacuo. The residue was dissolved in ethyl acetate and extracted with sodium carbonate solution and water. After drying the ethyl acetate portion over magnesium sulfate, the solvent was removed in vacuo to obtain N-[2-(ethylamino)ethyl]-p-toluenesulfonamide as a viscous oil which crystallized on standing. Analytical sample prepared from ether-hexane melted at 50°–53°C.

Anal. Calc'd for $C_{11}H_{18}N_2SO_2$: C, 54.52; H, 7.49; N, 11.56 Found: C, 54.37; H, 7.55; N, 11.35.

The hydrochloride was prepared from a portion of the base. Recrystallization from ethanol-diethyl ether afforded the hydrochloride, m.p. 139°–141°C.

Anal. Calc'd for $C_{11}H_{18}N_2SO_2 \cdot HCl$: C, 47.38; H, 6.87: N, 10.05; Cl, 12.72; S, 11.50. Found: C, 47.22; H, 6.92; N, 10.17; Cl, 12.77; S, 11.35.

EXAMPLE V

A solution of 13 grams of ψ-acid chloride of 0-(p-chlorobenzoyl)benzoic acid in 30 ml. of acetone was added dropwise to a stirred solution of 14 grams of N-[2-(ethylamino)ethyl]-p-toluenesulfonamide hydrochloride in 100 ml. of pyridine. The solution was refluxed for 1.75 hours then the solvent was removed in vacuo. The residue dissolved in ethyl acetate and extracted successively with water, and saturated sodium carbonate solution. After drying over magnesium sulfate, the ethyl acetate was removed in vacuo. The solid was slurried with ethyl acetate and separated. On recrystallization from ethyl acetate there was obtained 2-(p-chlorobenzoyl)-N-[2-(p-toluenesulfonamido)ethyl]-N-ethylbenzamide, m.p. 145°–147°C.

Anal. Calc'd for $C_{25}H_{25}N_2ClSO_4$: C, 61.91; H, 5.20; N, 5.78; Cl, 7.31; S, 6.61. Found: C, 61,95; H, 5.24; N, 5.73; Cl, 7.27; S, 6.41

EXAMPLE VI

Six grams of 2-(p-chlorobenzoyl)-N-[2-p-toluenesulfonamido)ethyl]-N-ethylbenzamide and 25 ml. of sulfuric acid were mixed together and heated in a steam bath for 15 minutes. The solution was left at room temperature for 17 hours then quenched with ice water. The mixture was extracted with ethyl acetate. The aqueous portion was cooled and made basic with 50% sodium hydroxide solution. The precipitated solid was separated and washed thoroughly with water. Recrystallization from ethyl acetate-hexane afforded 4'-chloro-2-(1-ethyl-2-imidazolin-2-yl) benzophenone, m.p. 132°–134°C.

Anal. Calc'd for $C_{18}H_{17}N_2ClO$: C, 69,13; H, 5.47; N, 8.96; Cl, 11.34. Found: C, 68.97; H, 5.43; N, 8.71; Cl, 11.45.

The hydrochloride was prepared by saturating an ethanol solution of the base with hydrogen chloride. The solvent was removed in vacuo. The residue was recrystallized from ethanolethyl acetate to obtain the hydrochloride, m.p. 232°–234°C.

Anal. Calc'd for $C_{18}H_{17}N_2ClO \cdot HCl$: C, 61.89; H, 5.19; N, 8.02; Cl, 20.30. Found: C, 61.72; H, 5.57; N, 8.00; Cl, 20.17.

Infra red absorption (KBr) 1658 cm$^{-1}$.
UV (95% EtOH) max 262 $\mu$ ($\epsilon$ = 16,400).

EXAMPLE VII

A solution of 37 grams of $\psi$-acid chloride of 0-benzoyl benzoic acid in 60 ml. of dichloromethane was added dropwise to a stirred solution of 38.5 grams of N-[2-(isopropylamino) ethyl]-p-toluenesulfonamide, 200 ml. of dichloromethane and 25 ml. of triethylamine. The mixture was refluxed for 3.5 hours. After cooling, the solution was extracted successively with water, 10% hydrochloric acid, and saturated sodium carbonate solution. The dichloromethane solution was dried over magnesium sulfate and the solvent evaporated in vacuo to a solid residue. On recrystallization from ethyl acetate there was obtained 2-benzoyl-N-[2-(p-toluenesulfonamido)ethyl]-N-isopropylbenzamide, m.p. 135°–137°C.

Anal. Calc'd for $C_{26}H_{28}N_2SO_4$: C, 67.24; H, 6.07; N, 6.02; S, 6.90. Found: C, 67.45; H, 5.97; N, 6.03; S, 6.35.

EXAMPLE VIII

Fifty-five grams of 2-benzoyl-N-[2-(P-toluenesulfonamido)ethyl]-N-isopropylbenzamide and 125 ml. of 90% (v/v) sulfuric acid were mixed together and heated in a steam bath for 45 minutes. The solution was left standing at room temperature for 18 hours. The mixture was quenched with ice water and extracted with ethyl acetate. The aqueous portion was cooled and made basic with 50% sodium hydroxide solution. The mixture was extracted with ethyl acetate. The ethyl acetate portion was dried over magnesium sulfate and evaporated to dryness. The residue was dissolved in ethanol and saturated with hydrogen chloride. The solution was evaporated to dryness. Ethyl acetate was added and re-evaporated. The solid was recrystallized from ethanolethyl acetate to obtain 2-(1-isopropyl-2-imidazolin-2-yl)benzophenone hydrochloride, m.p. 262°–264°C dec.

Anal. Calc'd for $C_{19}H_{20}N_2O \cdot HCl$: C, 69.39; H, 6.43; N, 8.52; Cl 10.79. Found: C, 69.44; H, 6.64; N, 8.67; Cl, 10.67.

Infra red absorption (Kbr) 1664 cm$^{-1}$.
UV (95% EtOH)$\lambda$ max 251.5 ($\epsilon$ = 15,900).

EXAMPLE IX

A solution 19 grams of p-toluenesulfonyl chloride in 40 ml. of pyridine was added in portions to a stirred solution of 27 grams of 2-methyl-1,2-diaminopropane in 50 ml. of pyridine. The mixture was stirred an additional 20 minutes then filtered to separate 2-methyl-1,2-diaminopropane dihydrochloride. The filtrate was evaporated to dryness in vacuo. The residue was triturated with hexane until it crystallized. On recrystallization from ethyl acetate there was obtained N-[2-(amino-2,2-dimethyl)ethyl]-p-toluenesulfonamide, m.p. 92°–95°C.

Anal. Calc'd for $C_{11}H_{18}N_2SO_2$: C, 54.52; H, 7.49; N, 11.56; S, 13.23. Found: C, 54.69, H, 7.83; N, 11.57; S, 1312.

EXAMPLE X

A solution of 25 grams of acetyl chloride in 50 ml. of dichloromethane was slowly added to a stirred solution of 60 grams of N-[2-(amino-2,2-dimethyl)ethyl]-p-toluenesulfonamide in 200 ml. of pyridine. The mixture was stirred an additional hour then evaporated to dryness. The residue was triturated with sodium carbonate and water. The solid was separated and dried. On recrystallization from ethyl acetate there was obtained N-[2-(acetamido-2,2-dimethyl)ethyl]-p-toluenesulfonamide, m.p. 175°–177°C.

Anal. Calc'd for $C_{13}H_{20}N_2SO_3$: C, 54.90; H, 7.09; N, 9.85; S, 11.27. Found: C, 54.90; H, 6.91; N, 9.94; S, 11.23.

EXAMPLE XI

One-hundred-sixty-five grams of N-[2-(acetamido-2,2-dimethyl)ethyl]-p-toluenesulfonamide were added in portions over 1.5 hours to a stirred suspension of 42 grams of lithium aluminum hydride in 2.5 liters of anhydrous ether. The mixture was refluxed 18 hours then decomposed by dropwise addition of water. The solvent was separated and the filter cake was extracted with hot ethyl acetate. The organic portions were combined and evaporated to an approximate volume of 750 ml. The solution was extracted with water then dried over magnesium sulfate. The solvent was removed in vacuo. The residue was triturated with hexane until it crystallized. On recrystallization from ethyl acetate-hexane, there was obtained N-[2-(ethylamino-2,2-dimethyl)ethyl]-p-toluenesulfonamide, m.p. 71°–73°C.

Anal. Calc'd for $C_{13}H_{22}N_2SO_2$: C, 57.74; H, 8.20; N, 10.36; S, 11.86. Found: C, 57.88; H, 8.56; N, 10.54; S, 11.86.

EXAMPLE XII

A solution of 260 grams of ψ-acid chloride of 0(p-chlorobenzoyl)benzoic acid in 500 ml. of dichloromethane was added to a stirred, refluxing solution of 250 grams on N-[2-(ethylamino-2,2-dimethyl)ethyl]-p-toluenesulfonamide, 1.5 liters of dichloromethane, and 170 ml. of triethylamine. The addition was completed over a 3 hour period and refluxing was continued for 18 hours. The solution was concentrated to about 1.5 liters and extracted with 10% hydrochloric acid. (Neutralization of acid extract afforded recovery of unreacted N-[2-(ethylamino-2,2-dimethyl)ethyl]-p-toluenesulfonamide). The dichloromethane solution was further extracted with sodium carbonate solution and water. After drying the dichloromethane portion over magnesium sulfate, the solution was evaporated to dryness. The solid residue was recrystallized from ethyl acetate to obtain 2-(p-chlorobenzoyl)-N-[1,1-dimethyl-2-(p-toluenesulfonamido)ethyl]-N-ethyl benzamide, m.p. 175°–176°C.

Anal. Calc'd for $C_{27}H_{29}N_2ClSO_4$: C, 63.20; H, 5.70: N, 5.46; Cl, 6.91; S, 6.25. Found: C, 62,97; H, 5.86; N, 5,40; S, 6.49; Cl, 6.49.

EXAMPLE XIII

One-hundred-ninety grams of 2-(p-chlorobenzoyl)-N-[1,1-dimethyl-2-(p-toluenesulfonamido)ethyl]-N-ethyl benzamide and 400 ml. of 90% (v/v) sulfuric acid were mixed together and heated in a steam bath for 45 minutes. The solution was left at room temperature for 21 hours, then quenched with 3 volumes of ice water. The mixture was extracted with dichloromethane. The aqueous portion was cooled and made basic with 50% sodium hydroxide solution. The mixture was extracted with dichloromethane. This solvent was removed in vacuo. The residue crystallized on standing overnight. A portion was recrystallized from diethyl ether-hexane to obtain 4'-chloro-2-(1-ethyl-5,5-dimethyl-2-imidazolin-2-yl)benzophenone, m.p. 85°–87°C.

Anal. Calc'd for $C_{20}H_{21}N_2ClO$: C, 70.47; H, 6.21; N, 8.22; Cl, 10.41. Found: C, 70.41; H, 6.30: N, 8.28; Cl, 10.81.

The hydrochloride was prepared by treating an ethanol solution of the base with hydrogen chloride and removing the solvent in vacuo. The residue was recrystallized from ethanolethyl acetate to obtain the hydrochloride, m.p. 263°–265°C with dec.

Anal. Calc'd for $C_{20}H_{21}N_2ClO \cdot HCl$: C, 63.66; H, 5.88; N, 7.42; Cl, 18.79. Found: C, 63,69; H, 5.89; N, 7.57; Cl, 18.56.

Infra red absorption (KBr) 1663 $cm^{-1}$.
UV (95% EtOH) λ max 260 μ (ε = 16,500).

The hydrochloride of the product of this Example XIII was subjected to testing for pharmacological activity. Test results in animals demonstrated several pharmacological activities including hypoglycemic activity, antireserpine activity and antiarrhythmic activity.

EXAMPLE XIV

A mixture of 50 grams of 0-(p-fluorobenzoyl)benzoic acid, 150 grams of thionyl chloride and 2 ml. of dimethyl formamide was refluxed for 4 hours. The excess thionyl chloride was evaporated. The residue was dissolved in benzene and evaporated in vacuo to obtain the ψ-acid chloride of 0-(p-fluorobenzoyl) benzoic acid.

A solution of 54 grams of the ψ-acid chloride from above in 200 ml. of dichloromethane was added to a stirred solution of N-[2[(ethylamino)-2,2-dimethyl ethyl]-p-toluenesulfonamide, 40 ml. of triethylamine and 300 ml. of dichloromethane. The mixture was refluxed for 18 hours. The solution was cooled and washed successively with water, 10% hydrochloric acid, saturated sodium carbonate solution, and water. After drying over magnesium sulfate, the dichloromethane was removed in vacuo. The residue was dissolved in ethyl acetate and left standing overnight. The precipitated solid was separated by filtration. On recrystallization from ethyl acetate-hexane there was obtained 2-(p-fluorobenzoyl)-N-[1,1-dimethyl-2-(p-toluenesulfonamido)ethyl]-N-ethylbenzamide, m.p. 154°–156°C.

Anal. Calc'd for $C_{27}H_{29}N_2FSO_4$: C, 65.31; H, 5.88; N, 5.64; S, 6.45. Found: C, 65.48; H, 6.10; N, 5.99; S, 6.52.

EXAMPLE XV

Fifteen grams of 2-(p-fluorobenzoyl)-N-[1,1-dimethyl-2-(p-toluenesulfonamido)ethyl]-N-ethylbenzamide and 50 ml. of 90% (v/v) sulfuric acid were mixed together and heated in a steam bath for one-half hour. The solution was left at room temperature for 20 hours, then diluted with ice water. The mixture was extracted with ethyl acetate. The aqueous portion was cooled and made basic with saturated sodium carbonate solution. The resulting mixture was extracted with ethyl acetate. The ethyl acetate portion was dried over magnesium sulfate then evaporated in vacuo. The residue was dissolved in ethanol and saturated with hydrogen chloride. The solvent was removed in vacuo. The residue was treated with ethyl acetate and left standing (weekend). The crystalline solid was separated by filtration. On recrystallization from ethanol-ethyl ether, there was obtained 4'-fluoro-2-(1-ethyl-5,5-dimethyl-2-imidazolin-2-yl)benzophenone hydrochloride, m.p. 262°–264°C.

Anal. Calc'd for $C_{20}H_{21}FN_2O \cdot HCl$: C, 66.57; H, 6.14; N, 7.77; Cl, 9.83; Found: C, 66.78; H, 6.21; N, 7.79; Cl, 9.70.

Infra red absorption (KBr) 1658 $cm^{-1}$.
UV (95% EtOH) max 252.5 μ (ε = 15,600).

The hydrochloride product of this Example XV was subjected to testing for pharmacological activity. Test results in animals demonstrated hypoglycemic activity.

EXAMPLE XVI

A mixture of 22.6 grams of 0-benzoyl benzoic acid, 30 ml. of thionyl chloride and 1 ml. of dimethylformamide was refluxed for 2 hours. The solution was evaporated to dryness. The residue was dissolved in benzene and evaporated. The residue was dissolved in 75 ml. of acetone and added slowly to a stirred solution of 25 g. N-[2-(ethylamino-2,2-dimethyl)ethyl]-p-toluenesulfonamide and 100 ml. of pyridine. The mixture was refluxed for 1.5 hours then evaoporated to dryness. The residue was shaken with ethyl acetate and water. The ethyl acetate portion was extracted successively with 10% hydrochloric acid, sodium carbonate solution and water. After drying over magnesium sulfate, the ethyl acetate portion was evaporated to dryness. The residue was triturated with ether. The solid was separated (anhydride of 0-benzoyl-benzoic acid) and the filtrate was evaporated leaving a solid residue. Recrystallization from ethyl acetate afforded 2-benzoyl-N-

[1,1-dimethyl-2-(p-toluenesulfonamido)ethyl]-N-ethyl benzamide, m.p. 157°–160°. The infra red spectrum indicated the presence of some 0-benzoyl benzoic acid anhydride impurity.

7.5 Grams of 2-benzoyl-N-[1,1-dimethyl-2-(p-toluenesulfonamido)ethyl]-N-ethyl benzamide and 25 ml. of 90% (v/v) sulfuric acid were mixed together and heated in a steam bath for one-half hour. The solution was left at room temperature 21 hours then quenched with ice water. The mixture was extracted with ethyl acetate. The aqueous portion was cooled and made basic with 50% sodium hydroxide solution. The resulting mixture was extracted with ethyl acetate. This extract was washed with water and dried over magnesium sulfate. The solvent was removed in vacuo. The residue was dissolved in 40 ml. of ethanol and treated with hydrogen chloride. The solvent was removed in vacuo. The residue was recrystallized from ethanol-ethyl acetate to obtain 2-(1-ethyl-5,5-dimethyl-2-imidazolin-2-yl)benzophenone hydrochloride, m.p. 240°–243°C.

Anal. Calc'd for $C_{20}H_{22}N_2O \cdot HCl$: C, 70.06; H, 6.76; N, 8.17; Cl, 10.34. Found: C, 69.80; H, 7.07; N, 8.14; Cl, 10.33.

Infra red absorption (KBr) 1666 $cm^{-1}$.

UV (EtOH) λ max 252 ($\epsilon$ = 15,300).

The hydrochloride product of this Example XVI was subjected to testing for pharmacological activity. Test results in animals demonstrated hypoglycemic activity.

EXAMPLE XVII

A solution of 125 grams of tosyl-DL-alanyl chloride (A. F. Beecham, J. Am. Chem. Soc., 79, 325–7) in 800 ml. of dichloromethane was added with stirring to 73 grams of anhydrous ethylamine and 400 ml. of dichloromethane in a reaction flask equipped with a dry ice condenser. The mixture was refluxed 4 hours after addition was completed. The reaction mixture was extracted with water then dried over magnesium sulfate. The solvent was removed in vacuo. The residue was slurried with diethyl ether and filtered to obtain tosyl-DL-alanine ethylamide, m.p. 106°–107°C.

Anal. Calc'd for $C_{12}H_{18}N_2SO_3$: C, 53.31; H, 6.71; N, 10.37; S, 11.86. Found: C, 53.22; H, 6.54; N, 10.25; S, 12.10.

EXAMPLE XVIII

Sixty-seven grams of tosyl-DL-alanine ethyl amide was added in portions to a stirred suspension of 25 grams of lithium aluminum hydride in 1.5 liters of anhydrous ether. Refluxing was continued for 19 hours. Excess lithium aluminum hydride was decomposed by dropwise addition of water. The mixture was filtered and the filter cake extracted with hot ethyl acetate. The organic portions were combined and evaporated to a volume of about 300 ml. The solution was washed with water then dried over magnesium sulfate. Evaporation of the solvent afforded an oil which began to crystallize on cooling. A portion was recrystallized from ether to obtain N-[2-(ethylamino-1-methyl)ethyl]-p-toluenesulfonamide, m.p. 69°–71°C.

Anal. Calc'd for $C_{12}H_{20}N_2SO_2$: C, 56.22; H, 7.87; N, 10.93; S, 12.51.

Found: C, 56.21; H, 7.87; N, 10.97; S, 12.75.

EXAMPLE XIX

A solution of 58 grams of ψ-acid chloride of 0-(p-chlorobenzoyl)benzoic acid, 400 ml. of dichloromethane, 52 g. of N-[2-(ethylamino-1-methyl)ethyl]-p-toluenesulfonamide and 50 ml. of triethylamine was stirred at refluxed for 3 hours. The cooled mixture was extracted successively with water, 15% hydrochloric acid, and sodium carbonate solution. After drying over magnesium sulfate, the dichloromethane was evaporated in vacuo. The residue was triturated with ether. The separated solid was recrystallized from ethyl acetate to obtain 2-(p-chlorobenzoyl-N-[2-methyl-2-(p-toluenesulfonamido)ethyl]-N-ethyl benzamide, m.p. 161°–163°C.

Anal. Calc'd for $C_{26}H_{27}N_2ClSO_4$: C, 62.58; H, 5.45; N, 5.61; Cl, 7.11.

Found: C, 62.66; H, 5.46; N, 5.31; Cl, 7.42.

EXAMPLE XX

Forty grams of 2-(p-chlorobenzoyl)-N-[2-methyl-2-(p-toluenesulfonamido)ethyl]-N-ethylbenzamide and 100 ml. of 90% (v/v) sulfuric acid were mixed together and heated in a steam bath for 45 minutes. After standing at room temperature 21 hours, the solution was quenched with 500 ml. of ice water. The mixture was extracted with dichloromethane. The aqueous portion was cooled and made basic with 50% sodium hydroxide solution. The mixture was extracted with ethyl acetate. The ethyl acetate portion was extracted with water then dried over magnesium sulfate. The solvent was removed in vacuo. The residue was dissolved in diethyl ether and treated with hydrogen chloride. The solid was separated and recrystallized from ethanol-ethyl acetate to obtain 4'-chloro-2-(1-ethyl-4-methyl-2-imidazolin-2-yl)benzophenone hydrochloride, m.p. 212°–214°C.

Anal. Calc'd for $C_{19}H_{19}ClN_2O \cdot HCl$: C, 62.81; H, 5.55; N, 7.71; Cl, 19.52.

Found: C, 62.72; H, 5.61; N, 7.51; Cl, 19.43.

Infra red absorption (KBr) 1661 $cm^{-1}$.

UV (95% EtOH) λ max 266 ($\epsilon$ = 16,200).

The hydrochloride product of this Example XIX was subjected to testing for pharmacological activity. Test results in animals demonstrated hypoglycemic activity and antiarrhythmic activity.

EXAMPLE XXI

Following the procedure of Example 15 but using 2-(p-bromobenzoyl)-N-[1,1-dimethyl-2-(p-toluenesulfonamido)ethyl]-N-ethylbenzamide, there is obtained 4'-bromo-2-(1-ethyl-5,5-dimethyl-2-imidazolin-2-yl)benzophenone hydrochloride having a melting point of 265°–266°C. The hydrochloride in animal tests demonstrated hypoglycemic activity.

EXAMPLE XXII

Following the procedure of Example 15 but using 2-(3,4-dichlorobenzoyl)-N-[1,1-dimethyl-2-(p-toluenesulfonamido) ethyl]-N-ethylbenzamide, there is obtained 3',4'-dichloro-2-(1-ethyl-5,5-dimethyl-2-imidazolin-2-yl)benzophenone hydrochloride having a melting point of 229°–231°C. The hydrochloride in animal tests demonstrated hypoglycemic activity and antireserpine activity.

EXAMPLE XXIII

Following the procedure of Example 15 but using 2-benzoyl-N-[2,-methyl-2(p-toluenesulfonamido)ethyl]-N-isopropylbenzamide, there is obtained 2-(1-isopropyl-4-methyl-2-imidazolin-2-yl)benzophenone hydrochloride having a melting point of 245°–247°C. The hydrochloride in animal tests demonstrated hypoglycemic activity.

EXAMPLE XXIV

Following the procedure of Example 12 but using 2-(p-chlorobenzoyl)-N-[2-methyl-2-(p-toluenesulfonamido)ethyl]-N-isopropylbenzamide, there is obtained 4'-chloro-2(1-isopropyl-4-methyl-2-imidazolin-2-yl)benzophenone having a melting point of 109°–112°C. The hydrochloride in animal tests demonstrated hypoglycemic activity.

EXAMPLE XXV

Following the procedure of Example 15 but using 2-(p-chlorobenzoyl)-N-[2-isopropyl-2(p-toluenesulfonamido)ethyl]-N-ethylbenzamide, there is obtained 4'-chloro-2-(1-ethyl-4-isopropyl-2-imidazolin-2-yl)benzophenone hydrochloride having a melting point of 178°–180°C. The hydrochloride in animal tests demonstrated hypoylycemic activity.

EXAMPLE XXVI

Following the procedure of Example 15 but using 2-benzoyl-N-[2-isopropyl-2(p-toluenesulfonamido)ethyl]-N-ethylbenzamide, there is obtained 2-(1-ethyl-4-isopropyl-2-imidazolin-2-yl)benzophenone hydrochloride having a melting point of 213°–215°C. The hydrochloride in animal tests demonstrated hypoglycemic activity.

EXAMPLE XXVII

Following the procedure of Example 15 but using 2-(p-chlorobenzoyl)-N-[1-methyl-2-(p-toluenesulfonamido)ethyl]-N-ethylbenzamide having a melting point of 134°–137°C, there is obtained 4'-chloro-2-(1-ethyl-5-methyl-2-imidazolin-2-yl)benzophenone hydrochloride having a melting point of 233°–235°C. The hydrochloride in animal tests demonstrated antiarrhythmic activity.

EXAMPLE XXVIII

Following the procedure of Example 15 but using 2-(p-chlorobenzoyl)-N-[2-[2-(p-toluenesulfonamide)ethyl]-N-n-propylbenzamide, there is obtained 4'-chloro-2-(1-n-propyl-2-imidazolin-2-yl)benzophenone, m.p. 131°–133°C.

EXAMPLE XXIX

Following the procedure of Example 15 but using 2-(p-chlorobenzoyl)-N-[2-methyl-2-p-toluenesulfonamido)ethyl]-N-ethylbenzamide having a melting point of 118°–121°C. and $[\alpha]_D^{24}$ + 11.99 (1.038, EtOH), there is obtained D (+) -4'-chloro-2-(1-ethyl-4-methyl-2-imidazolin-2-yl)benzopheonone hydrochloride, m.p. 221°–3°C., $[\alpha]_D^{24}$ + 48.23 (1.001, EtOH).

EXAMPLE XXX

Following the procedure of Example 15 but using 2-(p-fluorobenzoyl)-N-[2-(p-toluenesulfonamido)ethyl]-N-isopropylbenzamide, there is obtained 4'-fluoro-2-(1-isopropyl-2-imidazolin-2-yl)benzophenone hydrochloride, m.p. 272°–273°C.

EXAMPLE XXXI

Following the procedure of Example 15 but using 2-(p-toluoyl)-N-[2-(p-toluenesulfonamido)ethyl]-N-isopropylbenzamide there is obtained 2-(1-isopropyl-2-imidazolin-2-yl)-4'-methyl benzophenone, m.p. 87°–89°C.

EXAMPLE XXXII

Following the procedure of Example 15 but using 2-(p-trifluoromethylbenzoyl)-N-[2-(p-toluenesulfonamido)ethyl]-N-isopropylbenzamide, there is obtained 4'-trifluoromethyl-2-(1-isopropyl-2-imidazolin-2-yl)benzophenone hydrochloride, m.p. 215°–217°C.

EXAMPLE XXXIII

By analogous procedures the following compounds are prepared. In all of these compounds, $R_2$ is hydrogen.

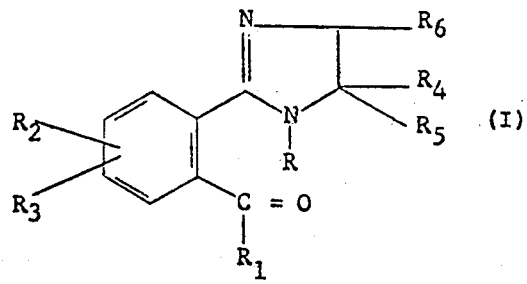

| | R | $R_1$ | $R_3$ | $R_4$ | $R_5$ | $R_6$ | M.P.,°C. |
|---|---|---|---|---|---|---|---|
| 1. | Isopropyl | 3,4-dichlorophenyl | H | H | H | H | 218–20. |
| 2. | Isopropyl | 4-bromophenyl | " | " | " | " | 253–55 |
| 3. | n-propyl | phenyl | " | " | " | " | 185–7 |
| 4. | n-propyl | 4-fluorophenyl | " | " | " | " | 212–15 |
| 5. | ethyl | phenyl | " | " | " | " | 199–201 |
| 6. | isopropyl | phenyl | 5-chloro | " | " | " | 123–5 |
| 7. | isopropyl | 3-chlorophenyl | H | " | " | " | 253–5 |
| 8. | isopropyl | 3,5-dichlorophenyl | " | " | " | " | 246–8 |
| 9. | isopropyl | 2-chlorophenyl | " | " | " | " | 138–40 |
| 10. | isopropyl | phenyl | | 4-chloro | " | " | 265–7 |
| 11. | ethyl | 3-chlorophenyl | H | Me | " | " | 208–10 |

Compounds 6 and 9 are the free base and the others are the hydrochloride.

EXAMPLE XXXIV

By analogous procedures the following compounds are prepared as the hydrochloride salt except when indicated.

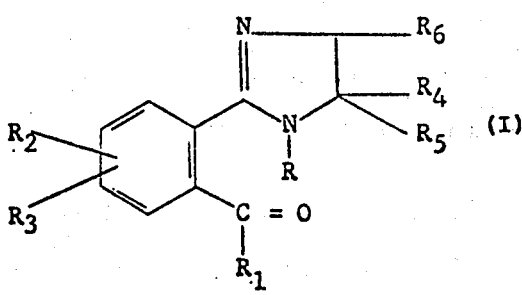

In all of these compounds, $R_2$, $R_3$, $R_4$ and $R_5$ are hydrogen.

|  | R | $R_1$ | $R_6$ | M.P.,°C. | $[\alpha]_D$ |
|---|---|---|---|---|---|
| 1. | ethyl | 4-chlorophenyl | methyl | 221–3 | — |
| 2. | isopropyl | 4-chlorophenyl | isopropyl | 102–04 | ± |
| 3. | isopropyl | phenyl | isopropyl | 62–4 | ± |
| 4. | ethyl | 4-fluorophenyl | isopropyl | 202–5 | ± |
| 5. | n-propyl | 4-chlorophenyl | methyl | 195–8 | ± |
| 6. | ethyl | phenyl | methyl | 216–18 | ± |
| 7. | ethyl | 4-fluorophenyl | methyl | 202–5 | ± |
| 8. | ethyl | 4-chlorophenyl | methoxy-methylene | 210–12 | ± |
| 9. | ethyl | 4-chlorophenyl | ethyl | 185–7 | ± |
| 10. | ethyl | phenyl | ethyl | 182–4 | ± |
| 11. | n-propyl | 4-chlorophenyl | methyl | 192–4 | + |
| 12. | n-propyl | phenyl | methyl | 193–6 | + |
| 13. | ethyl | 4-chlorophenyl | n-propyl | 167–9 | ± |
| 14. | ethyl | 4-fluorophenyl | n-propyl | 164–6 | ± |
| 15. | ethyl | phenyl | n-propyl | 148–50 | ± |
| 16. | ethyl | phenyl | isopropyl | 210–12 | + |
| 17. | ethyl | 4-chlorophenyl | isopropyl | Liquid | + |
| 18. | ethyl | 4-fluorophenyl | isopropyl | 191–3 | + |

Compounds 2, 3 and 17 are the free base and the others are the hydrochloride.

EXAMPLE XXXV

By analogous procedures the following compounds are prepared. In all of these compounds, $R_2$, $R_3$, $R_4$ and $R_5$ are hydrogen except that in compound 12, $R_3$ is 5-chloro.

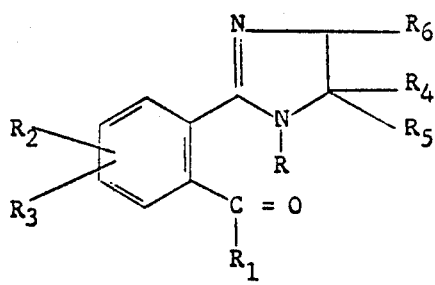

(I)

|  | R | $R_1$ | $R_6$ | $[\alpha]_D$ | M.P.,°C |
|---|---|---|---|---|---|
| 1. | ethyl | phenyl | methyl | — | 219–21 |
| 2. | ethyl | phenyl | methyl | + | 218–20 |
| 3. | methyl | phenyl | isopropyl | + | 171–3 |
| 4. | methyl | 4-chlorophenyl | isopropyl | + | 182–4 |
| 5. | ethyl | 4-fluorophenyl | isopropyl | — | 190–2 |
| 6. | ethyl | phenyl | isopropyl | — | 212–14 |
| 7. | ethyl | 4-chlorophenyl | isopropyl | — | 177–9 |
| 8. | methyl | phenyl | methyl | + | Liquid |
| 9. | methyl | 4-chlorophenyl | methyl | + | 230–32 |
| 10. | ethyl | phenyl | n-butyl | ± | 155–8 |
| 11. | ethyl | phenyl | n-propyl | + | 179–81 |
| 12. | ethyl | phenyl | methyl | + | 126–8 |
| 13. | ethyl | 3-chlorophenyl | isopropyl | + | 210–12 |
| 14. | ethyl | phenyl | n-propyl | — | 178–80 |
| 15. | ethyl | 2-chlorophenyl | methyl | ± | 189–92 |
| 16. | ethyl | 3-chlorophenyl | methyl | — | 200–202 |
| 17. | ethyl | 3-chlorophenyl | methyl | + | 194–6 |
| 18. | ethyl | 2-chlorophenyl | methyl | + | 226–8 |

Compounds 8 and 12 are the free base and the others are the hydrochloride.

The new compounds of formula I and their pharmaceutically acceptable salts possess pharmacological activity. In particular they generally demonstrate one or more of the following activities: hypoglycemic activity, antireserpine activity, antiulcerogenic activity and antiarrhythmic activity, when tested in animals. The new compounds of formula II possess utility as intermediates for the preparation of the pharmacologically active compounds of formula I by the process described above.

The test for hypoglycemic activity was conducted as follows

Male rats weighing 170–200 grams are fasted overnight, a control blood sample is taken from the tail and a test dose of 60 mg/kg is administered by stomach tube. Subsequent blood samples are taken at hourly intervals for five hours. In general, a compound is considered active if a depression in blood sugar approximating 20% is observed for at least three of the five hour test period.

The test for antireserpine activity was conducted as follows

Compounds at graded dose levels are administered orally (or intraperitoneally) to groups of six mice (3 males and 3 females) at 2 dose levels, 1 and 10 mg/kg. One hour later (or one-half hour later if the compound was administered i.p.) the animals are challenged with reserpine, 2.5 mg/kg i.p. The degree of ptosis for each eye is determined at 1 hr. post-treatment. Both a Tween 80 control group and two imipramine control groups (1 and 10 mg/kg) are run simultaneously. Mean ptotic scores are calculated for all groups. A compound is considered active if the mean ptotic score is 2 or less at either or both of the 2 doses tested.

The test for antiulcerogenic activity was conducted as follows

Male Charles River rats weighing between 120–160 gm. are deprived of food for 18 hr. with water ad lib. The rats are divided into groups of ten and dosed by oral route with test compound (base), or vehicle control, 1% methyl-cellulose, in a volume of 5 ml/kg. Immediately after dosing the animals are inserted into aluminum restraining tubes measuring 1⅝ inches in diameter by 8 inches and placed in the cold (4 ± 1°C.). After 180 min. the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa are counted by visual observation and recorded; however, since these numbers are so variable, only the incidence of ulcer (i.e., the number of rats with ulcers) are used for statistical evaluation.

The test for reserpine hypothermia was conducted as follows

Groups of male mice, 17–22 grams, are dosed with reserpine, 2.0 mg/kg. S.C. Four hours later, the rectal temperature of each mouse is measured with a thermocouple. The mice are then challenged orally with the test compound at graded dose levels and the rectal temperature measured every half hour for the following two hours or longer if necessary to show peak effect. The rise in rectal temperature produced by the drug is then compared graphically with that of the control group.

The pharmacological test results are summarized in the following Table I. A plus sign indicates activity, a minus sign indicates lack of activity at the particular dose level in the particular test and a blank indicates that the compound was not tested for the particular indication.

TABLE I

| Example | Hypoglycemic Activity | Antireserpine Activity | Antiulcer Activity | Antiarrhythmic Activity | Reserpine Hypothermia |
|---|---|---|---|---|---|
| 3 | + | + | + | + | + |
| 6 | + | + | + | | + |
| 8 | + | + | + | + | |
| 13 | + | + | | + | + |
| 15 | + | − | | | |
| 16 | + | + | | | |
| 20 | + | − | | + | |
| 21 | + | | | | |
| 22 | + | + | | | |
| 23 | + | + | + | | − |
| 24 | + | + | | | − |
| 25 | + | − | | + | − |
| 26 | + | | + | + | |
| 27 | + | + | + | + | |
| 28 | + | + | | + | + |
| 29 | + | | + | | − |
| 30 | − | + | + | − | + |
| 31 | − | + | + | | |
| 32 | − | + | + | | − |
| 33-1 | + | + | * | + | + |
| 33-2 | − | + | + | | + |
| 33-3 | + | − | | | − |
| 33-4 | − | + | + | | + |
| 33-5 | + | + | | | + |
| 33-6 | + | + | | | |
| 33-7 | + | + | + | | + |
| 33-8 | + | + | | | − |
| 33-9 | − | + | + | | |
| 33-10 | − | + | − | | |
| 33-11 | + | + | + | | + |
| 34-1 | − | + | + | | + |
| 34-2 | − | − | + | + | − |
| 34-3 | − | + | + | | − |
| 34-4 | + | − | | | − |
| 34-5 | + | + | | + | |
| 34-6 | + | − | | | |
| 34-7 | + | + | | | |
| 34-8 | + | + | | + | |
| 34-9 | + | + | + | | |
| 34-10 | + | + | | | |
| 34-11 | + | + | + | | − |
| 34-12 | + | + | + | | |
| 34-13 | + | + | + | | |
| 34-14 | + | + | + | + | |
| 34-15 | + | + | + | | |
| 34-16 | + | + | | | |
| 34-17 | + | + | | | |
| 34-18 | + | + | | | |
| 35-1 | + | + | | | |
| 35-2 | + | + | | | |
| 35-3 | + | | | + | |
| 35-4 | Toxic * | + | | | |
| 35-5 | + | + | + | | |
| 35-6 | + | + | | | |
| 35-7 | + | − | + | − | − |
| 35-8 | + | − | | | |
| 35-9 | + | + | | | |
| 35-10 | + | + | | | |
| 35-11 | + | − | | | |
| 35-12 | + | − | | | |
| 35-13 | + | + | | | − |
| 35-14 | + | − | | | − |
| 35-15 | Toxic ** | − | | | − |
| 35-16 | + | + | + | | + |
| 35-17 | + | + | + | | + |
| 35-18 | + | − | + | | − |

* Three-quarters of the rats died at a dose of 60 mg/kg.
** One-quarter of the rats died at a dose of 60 mg/kg.

In addition to the above pharmacological results, the compounds of Examples 3 and 29 were evulated as gastric antisecretory compounds in the pylorus ligated rat test and found to be active at 25 to 12.5 mg base/kg and 3 mg base/kg. This suggests that the antiulcer activity may be due to the inhibition of gastric secretion.

It will be apparent to the skilled chemist that the compounds of formula I, their acid addition salts and compounds of formula II possess an asymmetric structure when (i) $R_4$ is hydrogen and $R_5$ is (lower)alkyl or (ii) $R_6$ is (lower)alkyl. Such compounds with an asymmetric structure can exist as different optically active enantiomers. It is to be understood that the invention provides the compounds of asymmetric structure as the individual enantiomers and as mixtures of the enantiomers, for example, racemic mixtures. Individual enantiomers can be obtained in known manner by resolving a mixture of enantiomers or by preparation from an optically active starting material. Optically active starting materials in turn may be obtained by resolution of a mixture of steroisomers or by a chemical reaction using an optically active reactant. The compounds of formula I and their acid addition salts can be obtained as racemic mixtures or as individual enantiomers. The optically active products are preferably obtained by using an optically active compound of formula II as starting material.

The compounds of formula I may be obtained in free base form or as an acid addition salt. Examples of pharmaceutically acceptable acid addition salts include the sulphate, hydrochloride, hydrobromide, hydroiodide, nitrate, phosphate sulphonate (such as the methanesulphonate and p-toluenesulphonate), acetate, maleate, fumarate, tartrate and formate.

The invention also includes pharmaceutical compositions containing an active ingredient a compound of formula I or its pharmaceutically acceptable acid addition salt and a pharmaceutically acceptable carrier. Any suitable carrier known in the art can be used to prepare the pharmaceutical compositions. In such a composition, the carrier may be solid. Suitable solid carriers are magnesium carbonate, magnesium stearate; talc, sugar, lactose, pectin, dextrin, starch, gelatin, tragacanth, methyl, cellulose, sodium carboxymethyl cellulose, a low melting was, and cocoa butter. Sterile liquid form compositions include sterile solutions and suspensions. The active ingredient can be dissolved or suspended in a pharmaceutically acceptable sterile liquid carrier, such as sterile water, sterile organic solvent or a mixture of both.

We claim:

1. A process for the preparation of compounds of the formula

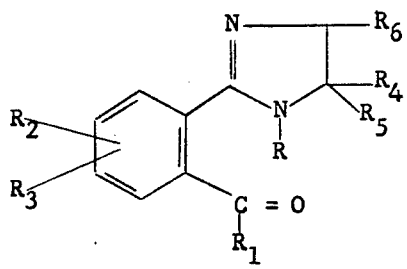

wherein R is (lower)alkyl; $R_1$ is selected from the group consisting of phenyl, monohalophenyl, dihalophenyl, mono(lower)alkylphenyl, di(lower)-alkylphenyl, trifluoromethylphenyl, mono(lower)alkoxyphenyl, di(lower)alkoxyphenyl, thienyl, pyridyl, furyl, and tetrahydro-2-naphthyl; $R_2$ is selected from the group consisting of hydrogen, halogen, amino, (lower)alkylamino, (lower)alkyl and (lower) alkoxy; $R_3$ is hydrogen when $R_2$ and $R_3$ are dissimilar and when $R_2$ and $R_3$ are the same they are both selected from the group consisting of hydrogen, halogen, (lower)alkyl and (lower)alkoxy; $R_4$ and $R_5$ are each hydrogen or lower alkyl and attached to the same carbon atom; and $R_6$ is hydrogen or (lower)alkyl which comprises heating a compound of the formula

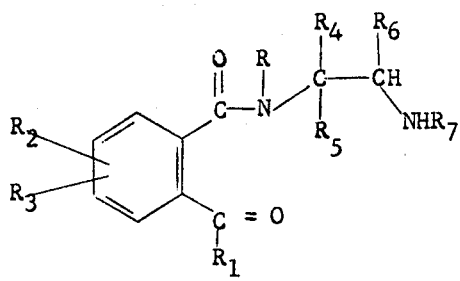

wherein R, $R_1$, $R_2$, $R_3$, $R_4$, $R_5$ and $R_6$ are as defined above and $R_7$ is selected from the group consisting of lower alkylsulfonyl, phenylsulfonyl, monohalophenysulfonyl, dihalophenylsulfonyl, mono(lower)alkylphenylsulfonyl, di(lower)alkylphenylsulfonyl and lower alkoxyphenylsulfonyl, on a steam bath with sulfuric acid of from about 90° to about 100° concentration.

2. Compounds of the formula

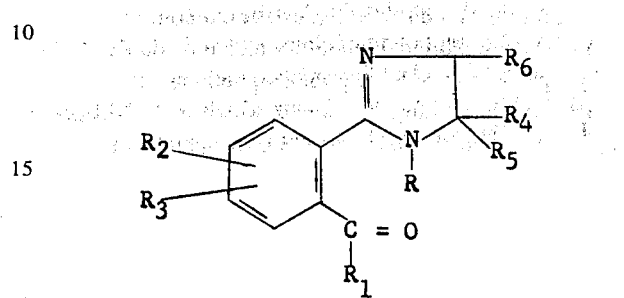

wherein R is (lower)alkyl; $R_1$ is selected from the group consisting of phenyl, monohalophenyl, dihalophenyl, mono(lower)alkylphenyl, di(lower)alkylphenyl, trifluoromethylphenyl, mono(lower) alkoxyphenyl, di(lower)alkoxyphenyl; $R_2$ is selected from the group consisting of hydrogen, halogen, amino (lower)alkylamino, (lower)alkyl and (lower) alkoxy; $R_3$ is hydrogen when $R_2$ and $R_3$ are dissimilar and when $R_2$ and $R_3$ are the same they are both selected from the group consisting of hydrogen, halogen, (lower) alkyl and (lower)alkoxy; $R_4$ and $R_5$ are each hydrogen or lower alkyl and attached to the same carbon atom; and $R_6$ is hydrogen or (lower)alkyl, or the pharmaceutically acceptable acid addition salt of such a compound.

3. The compound of claim 2 which is 4'-chloro-2-(1-ethyl-5,5-dimethyl-2-imidazolin-2-yl)benzophenone or a pharmaceutically acceptable acid addition salt.

4. The compound of claim 2 which is 4'fluoro-2-(1-ethyl-5,5-dimethyl-2-imidazolin-2-yl)benzophenone or a pharmaceutically acceptable acid addition salt.

5. The compound of claim 2 which is 2-(1-ethyl-5,5-dimethyl-2-imidazolin-2-yl)benzophenone or a pharmaceutically acceptable acid addition salt.

6. The compound of claim 2 which is 4'-chloro-2-(1-ethyl-4-methyl-2-imidazolin-2-yl)benzophenone or a pharmaceutically acceptable acid addition salt.

7. The compound of claim 2 which is 4'-bromo-2-(1-ethyl-5,5-dimethyl-2-imidazolin-2-yl)benzophenone or a pharmaceutically acceptable acid addition salt.

8. The compound of claim 2 is 3',4'-dichloro-2-(1-ethyl-5,5-dimethyl-2-imidazolin-2-yl)benzophenone or a pharmaceutically acceptable acid addition salt.

9. The compound of claim 2 which is 2-(1-isopropyl-4-methyl-2-imidazolin-2-yl)benzophenone or a pharmaceutically acceptable acid addition salt.

10. The compound of claim 2 which is 4'chloro-2(1-isopropyl-4-methyl-2-imidazolin-2-yl)benzophenone or a pharmaceutically acceptable acid addition salt.

11. The compound of claim 2 which is 4'-chloro-2-(1-ethyl-4-isopropyl-2-imidazolin-2-yl)benzophenone or a pharmaceutically acceptable acid addition salt.

12. The compound of claim 2 which is 2-(1-ethyl-4-isopropyl-2-imidazolin-2-yl)benzophenone or a pharmaceutically acceptable acid addition salt.

13. The compound of claim 2 which is 4'-chloro-2-(1-ethyl-5-methyl-2-imidazolin-2-yl)benzophenone or a pharmaceutically acceptable acid addition salt.

14. The compound of claim 2 which is 4'-chloro-2-(1-isopropyl-2-imidazolin-2-yl)benzophenone.

15. The compound of claim 2 which is 4'-chloro-2-(1-ethyl-2-imidazolin-2-yl)benzophenone.

16. The compound of claim 2 which is 2-(1-isopropyl-2-imidazolin-2-yl)benzophenone.

17. The compound of claim 2 which is 4'-chloro-2-(1-n-propyl-2-imidazolin-2-yl)benzophenone.

18. The compound of claim 2 which is 4'-fluoro-2-(1-isopropyl-2-imidazolin-2-yl)benzophenone.

19. The compound of claim 2 which is 2-(1-isopropyl-2-imidazolin-2-yl)-4'-methyl benzophenone.

20. The compound of claim 2 which is 4'-trifluoromethyl-2-(1-isopropyl-2-imidazolin-2-yl)benzophenone.

21. The compound of claim 2 which is L-(−)-2-(1-ethyl-4-methyl-2-imidazolin-2-yl)benzophenone.

22. The compound of claim 2 which is L-(−)-2-(1-ethyl-4-isopropyl-2-imidazolin-2-yl)benzophenone.

23. The compound of claim 2 which is D-(+)-2-(1-ethyl-4-isopropyl-2-imidazolin-2-yl)benzophenone.

24. The compound of claim 2 which is D-(+)-4'-chloro-2-(1,4-dimethyl-2-imidazolin-2-yl)benzophenone.

25. D-(+)-2-(1-ethyl-4-isopropyl-2-imidazolin-2-yl)-4'-fluoro-benzophenone, hydrochloride.

* * * * *

UNITED STATES PATENT AND TRADEMARK OFFICE
CERTIFICATE OF CORRECTION

PATENT NO. : 3,931,218
DATED : January 6, 1976
INVENTOR(S) : Sulkowski et al

It is certified that error appears in the above–identified patent and that said Letters Patent are hereby corrected as shown below:

Column 2, line 11: patent number should read "3,803,155."

Column 2, line 55: RHN should be connected to the rest of the structure:

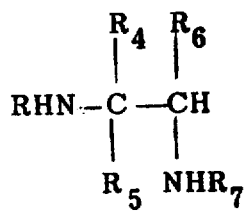

[SEAL]

Attest:

Attesting Officer

Signed and Sealed this

Nineteenth Day of February 1980

SIDNEY A. DIAMOND

Commissioner of Patents and Trademarks